United States Patent
Girgis et al.

(10) Patent No.: US 9,956,552 B2
(45) Date of Patent: *May 1, 2018

(54) REGENERATION OF ACIDIC IONIC LIQUID WITHOUT ADDITION OF A HYDROGENATION CATALYST

(71) Applicant: Chevron U.S.A. Inc., San Ramon, CA (US)

(72) Inventors: Michael John Girgis, Richmond, CA (US); Huping Luo, Richmond, CA (US); Bong Kyu Chang, Novato, CA (US); Hye-Kyung Timken, Albany, CA (US); Steven Xugi Song, Albany, CA (US); Michael Sean Driver, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 70 days.

This patent is subject to a terminal disclaimer.

(21) Appl. No.: 15/010,168

(22) Filed: Jan. 29, 2016

(65) Prior Publication Data

US 2017/0216827 A1 Aug. 3, 2017

(51) Int. Cl.
*C07C 2/58* (2006.01)
*B01J 31/40* (2006.01)
(Continued)

(52) U.S. Cl.
CPC ........... *B01J 31/40* (2013.01); *B01J 31/0284* (2013.01); *B01J 35/12* (2013.01); *B01J 38/10* (2013.01);
(Continued)

(58) Field of Classification Search
USPC .................... 585/727; 502/100, 150
See application file for complete search history.

(56) References Cited

U.S. PATENT DOCUMENTS 2,910,513 A 10/1959 Ridgway et al.
7,651,970 B2 1/2010 Elomari et al.
(Continued)

FOREIGN PATENT DOCUMENTS

GB 1416194 12/1975

OTHER PUBLICATIONS

Pines, H., The Chemistry of Catalytic Hydrocarbon Conversions, Wiley, 1981, p. 39ff.
(Continued)

*Primary Examiner* — James E McDonough
(74) *Attorney, Agent, or Firm* — Susan M. Abernathy (57) ABSTRACT

We provide a process for regenerating a spent acidic ionic liquid, comprising contacting the spent acidic ionic liquid with hydrogen and without an addition of a hydrogenation catalyst; wherein a conjunct polymer content is decreased in the spent acidic ionic liquid to produce regenerated acidic ionic liquid. We also provide a process for making an alkylate gasoline blending component, comprising: a) alkylating a mixture of isoparaffins and olefins using an acidic ionic liquid and an alkyl halide or a hydrogen halide, wherein a conjunct polymer accumulates in a spent acidic ionic liquid; and b) feeding the spent acidic ionic liquid and a hydrogen, and without an addition of a hydrogenation catalyst, to a regeneration reactor operated under selected hydrogenation conditions to produce a regenerated acidic ionic liquid that is used for the alkylating, wherein the conjunct polymer in the regenerated acidic ionic liquid is decreased by at least 50 wt %.

23 Claims, 8 Drawing Sheets

(51) Int. Cl.
    *B01J 31/02*     (2006.01)
    *B01J 38/10*     (2006.01)
    *C07C 2/62*     (2006.01)
    *C10L 1/06*     (2006.01)
    *C10G 29/20*     (2006.01)
    *C10G 45/60*     (2006.01)
    *C10G 47/02*     (2006.01)
    *C10G 50/00*     (2006.01)
    *B01J 35/12*     (2006.01)

(52) U.S. Cl.
    CPC .............. *C07C 2/62* (2013.01); *C10G 29/205* (2013.01); *C10G 45/60* (2013.01); *C10G 47/02* (2013.01); *C10G 50/00* (2013.01); *C10L 1/06* (2013.01); *B01J 2231/44* (2013.01); *C07C 2531/02* (2013.01); *C10L 2270/023* (2013.01); *C10L 2290/12* (2013.01)

(56) References Cited

U.S. PATENT DOCUMENTS

| | | |
|---|---|---|
| 7,674,739 B2 | 3/2010 | Elomari et al. |
| 7,691,771 B2 | 4/2010 | Harris et al. |
| 7,732,363 B2 | 6/2010 | Elomari et al. |
| 9,802,186 B2 * | 10/2017 | Luo .......................... B01J 31/40 |
| 2007/0142213 A1 * | 6/2007 | Elomari ............... B01J 31/0284 502/53 |
| 2007/0249486 A1 | 10/2007 | Elornari |
| 2014/0039230 A1 | 2/2014 | Timken |

OTHER PUBLICATIONS

Pines, H., Chemtech, 1982, p. 150.
Miron, S. and Lee, R.J., J. Chem. Eng. Data, 1963, p. 150.
Ingred M. Angulo et. al., Journal of Molecular Catalysis A: Chemical 202 (2003) 97-106.
U.S. Appl. No. 14/481,145, filed Sep. 9, 2014.
PCT/US2017/013858 International Search Report.
Gadalla, A.M., T.C. Chan, and R.G. Anthony, Int. J. Chem. Kinet. 15,759 (1983).
Sano, T., O. Kiyomi, H. Hagiwara, H. Takaya, J Shoji, and K. Matsuzaki, J. Mol. Catal., 40, 113 (1987.
Garwood, William E. and Dwyer Francis G., Shape Selective Catalysis in Industrial Applications, 146-147.

* cited by examiner

REGENERATION OF ACIDIC IONIC LIQUID WITHOUT ADDITION OF A HYDROGENATION CATALYST

This application is related to a co-filed application titled "REACTOR FOR HOMOGENEOUS REGENERATION OF SPENT IONIC LIQUID", herein incorporated in its entirety.

TECHNICAL FIELD

This application is directed to a process for regenerating a spent acidic ionic liquid without the addition of a hydrogenation catalyst. This application is also directed to a process for making an alkylate gasoline blending component including feeding a spent acidic ionic liquid and hydrogen to a regeneration reactor, without the addition of any solid hydrogenation catalyst to the regeneration reactor.

BACKGROUND

Improved processes are needed for regenerating spent acidic ionic liquids. Earlier processes have required significant quantities of hydrogenation catalysts to perform the hydro-regeneration. Hydrogenation catalysts need to be periodically replaced and/or regenerated, and they can be costly to purchase, handle, and dispose of.

SUMMARY

This application provides a process for regenerating a spent acidic ionic liquid, comprising contacting the spent acidic ionic liquid with hydrogen and without an addition of a hydrogenation catalyst; wherein a content of a conjunct polymer is decreased in the spent acidic ionic liquid to produce a regenerated acidic ionic liquid.

This application also provides a process for making an alkylate gasoline blending component, comprising:
  a. alkylating a mixture of one or more $C_4$-$C_7$ isoparaffins and one or more $C_2$-$C_6$ olefins in a presence of an acidic ionic liquid and an alkyl halide or a hydrogen halide, to produce the alkylate gasoline blending component, wherein a conjunct polymer is accumulated in a spent acidic ionic liquid;
  b. feeding the spent acidic ionic liquid and a hydrogen, and without the addition of a hydrogenation catalyst, to a regeneration reactor operated under hydrogenation conditions including a temperature from 100° C. to 350° C. and a pressure from 50 to 5000 psig (445 to 34600 kpa), wherein a content of the conjunct polymer is decreased by at least 50 wt % in the spent acidic ionic liquid and the spent acidic ionic liquid becomes a regenerated acidic ionic liquid that is used as a catalyst for the alkylating.

The present invention may suitably comprise, consist of, or consist essentially of, the elements in the claims, as described herein.

GLOSSARY

"Acidic ionic liquid" refers to materials consisting entirely of ions, that can donate a proton or accept an electron pair in reactions, and that are liquid below 100° C.

"Spent" refers to a less active catalytic material that has been contaminated during use, typically with conjunct polymer.

"Addition" refers to a purposeful step of adding a different material, e.g., a hydrogenation catalyst, to a vessel used for the contacting.

"Hydrogenation" refers to a chemical reaction between molecular hydrogen ($H_2$) and another compound or element to reduce or saturate organic compounds. For example, hydrogenation reduces double and triple bonds in hydrocarbons.

"Hydrogenation catalyst" refers to a metal-containing material that catalyzes hydrogenation of organic compounds.

"Periodic Table" refers to the version of the IUPAC Periodic Table of the Elements dated Jun. 22, 2007, and the numbering scheme for the Periodic Table Groups is as described in Chemical And Engineering News, 63(5), 27 (1985).

"Conjunct polymer" refers to poly-unsaturated cyclic, polycyclic, and acyclic molecules formed by concurrent acid-catalyzed reactions including, among others, polymerization, alkylation, cyclization, and hydride transfer reactions. Conjunct polymers contain double and conjugated double bonds in intricate structures containing a combination of cyclic and acyclic skeletons. Examples of conjunct polymers are described by Miron et al. (Journal of Chemical And Engineering Data, 1963) and Pines (Pines, H., The Chemistry of Catalytic Hydrocarbon Conversions, Wiley, 1981, p. 39ff).

"Hydrocracking" refers to a process in which hydrogenation and dehydrogenation accompanies the cracking/fragmentation of hydrocarbons, e.g., converting heavier hydrocarbons into lighter hydrocarbons, or converting aromatics and/or cycloparaffins(naphthenes) into non-cyclic branched paraffins.

"Noble metal" refers to a metal that is resistant to corrosion and oxidation in moist air (unlike most base metals). Examples of noble metals are ruthenium, rhodium, palladium, silver, osmium, iridium, platinum, and gold.

DETAILED DESCRIPTION

Hydrogenation is known to be an effective method used to regenerate spent acidic ionic liquids, but the processes known previously all required the addition of a hydrogenation catalyst to reduce a conjunct polymer in the spent acidic ionic liquid.

Hydrogenation Catalysts:

In conventional hydrogenation processes, significant quantities of hydrogenation catalysts are added, along with $H_2$, to the organic compounds to be reduced or saturated. The amount of the hydrogenation catalyst that is required to be added depends to a large extent on the metals present in the hydrogenation catalyst, but typically the hydrogenation catalyst is added in amounts greater than 5 wt % of the organic compounds being treated. The amount of the metal that needed to be used in the past for the effective hydrogenation of a spent acidic ionic liquid was added in excess to the concentration of the conjunct polymers present in the spent catalyst. Platinum, palladium, rhodium, and ruthenium can form highly active hydrogenation catalysts, which can operate at lower temperatures and lower pressures of $H_2$ compared to other metals. Non-precious metal hydrogenation catalysts, especially those based on nickel (such as Raney-nickel and Urushibara-nickel) have also been developed as economical alternatives, but they are often less active and require higher temperatures. The Raney-nickel catalyzed hydrogenations also require high pressures.

Conventional hydrogenation catalysts can comprise at least one metal selected from the group consisting of elements from Group 6 and Groups 8 through 10 of the Periodic Table. Hydrogenation catalysts can comprise at least one Group 6 metal and at least one metal selected from Groups 8 through 10 of the Periodic Table. For example, the metal can be selected from the group consisting of nickel (Ni), palladium (Pd), platinum (Pt), cobalt (Co), iron (Fe), chromium (Cr), molybdenum (Mo), tungsten (W), and mixtures thereof. Exemplary mixtures of metals that have been used in hydrogenation catalysts include Ni/Mo/W, Ni/Mo, Ni/W, Co/Mo, Co/W, Co/W/Mo, Ni/Co/W/Mo, and Pt/Pd. Exemplary metal combinations used in hydrogenation catalysts include Ni/Mo/W, Ni/Mo, Ni/W, Co/Mo, Co/W, Co/W/Mo and Ni/Co/W/Mo. Hydrogenation catalysts can be heterogenous or homogeneous. Heterogenous hydrogenation catalysts are in a different phase from the unsaturated organic compounds to be reduced or saturated. Typical examples of heterogeneous hydrogenation catalysts involve a solid catalyst with the unsaturated organic compounds being either liquids or gases. The unsaturated organic compounds are chemisorbed onto the heterogeneous hydrogenation catalyst, and hydrogen forms surface hydrides from which hydrogen can be transferred to the chemisorbed unsaturated organic compounds. Heterogeneous hydrogenation catalysts can be affected by their supports, i.e. the material upon which the heterogeneous hydrogenation catalyst is bound.

Homogeneous hydrogenation catalysts dissolve in the solvent that contains the unsaturated organic compounds to be reduced or saturated. Illustrative homogeneous hydrogenation catalysts include the rhodium-based compound known as Wilkinson's catalyst and the iridium-based Crabtree's catalyst.

Unlike earlier known processes used for regenerating acidic ionic liquids by hydrogenation, the process for regenerating a spent acidic ionic liquid described herein is done without the addition of a hydrogenation catalyst. Only the spent acidic ionic liquid is contacted with the hydrogen, and the conjunct polymer is reduced sufficiently to produce a regenerated acidic ionic liquid.

In one embodiment, no drying or reducing of the spent acidic ionic liquid is done before the contacting.

Contacting Conditions:

The conditions used for the contacting include a temperature less than 400° C. (752° F.). In one embodiment, the temperature is from 100° C. (212° F.) to 350° C. (662° F.).

The conditions used for the contacting include sufficient mixing to contact the spent acidic ionic liquid with hydrogen to produce the regenerated acidic ionic liquid. The sufficient mixing can be done using any equipment in the vessel that provides effective mixing, such as agitating, baffling, stirring, shaking, bubbling, vortexing, whisking or any other methods (or combinations thereof) known to produce the sufficient mixing. Examples of equipment that can be used to provide effective mixing include baffles, paddles, agitators, stirrers, nozzles, screens, filters, vibrators, vortex mixers, gas injectors, dispersers, spargers, and combinations thereof. In one embodiment, the contacting occurs in a vessel with an agitation rate of 50 to 2500 rpm.

The conditions for the contacting include an adequate supply of hydrogen to produce the regenerated acidic ionic liquid. In one embodiment, the contacting occurs in a vessel fed with hydrogen gas and the vessel having a pressure greater than 300 kpa. In one embodiment, the contacting occurs in a vessel under a pressure of 50 to 5000 psig (445 to 34600 kpa). Other ranges of pressure in the vessel during the contacting that can be used include 200 to 4000 psig (1480 to 27700 kpa), or 400 to 3000 psig (2860 to 20800 kpa).

The regenerated acidic ionic liquid can be produced over a wide range of times, depending on the contacting conditions used. Generally, the contacting time is greater than 1 hour. In one embodiment, the contacting time is from 2 to 50 hours.

In one embodiment, paraffinic light gases are formed during the contacting. These light gases can be entirely non-olefinic, and may comprise $C_2$-$C_4$ alkanes, such as ethane, propane, i-butane, and n-butane.

In one embodiment, an extracted conjunct polymer naphtha having between 5 and 30 carbon atoms can be produced by the contacting. In one embodiment, the extracted conjunct polymer naphtha has a final boiling point less than 246° C. (475° F.), a Bromine Number of 5 or less, and at least 30 wt % naphthenes. In one embodiment, the extracted conjunct polymer naphtha has at least 60 wt % carbon numbers in a range of $C_5$ through $C_{10}$. Extracted conjunct polymer naphthas made by contacting a spent acidic ionic liquid and hydrogen with the addition of a solid noble metal hydrogenation catalyst are disclosed in U.S. Pat. No. 8,704, 018. In one embodiment, the extracted conjunct polymer naphtha is mixed with an effluent from an alkylation reactor to make a blended alkylate gasoline.

In one embodiment, no solids are added or formed in a vessel used for the contacting.

In one embodiment, hydrogen chloride is formed during the contacting. The hydrogen chloride can be dissolved into the spent acidic ionic liquid. In one embodiment, the acidity of the spent acidic ionic liquid can be modulated by an amount of hydrogen chloride in the vessel used for the contacting. In one embodiment, the amount of the hydrogen chloride in the spent acidic ionic liquid is maintained at a level that increases a rate of decrease of the content of the conjunct polymer.

Acidic Ionic Liquids:

Acidic ionic liquids can be used as catalysts for various types of hydrocarbon conversions. Also, the regenerated acidic ionic liquid can also be effective for catalyzing a hydrocarbon conversion. Examples of these hydrocarbon conversions include: an alkylation, a polymerization, a dimerization, an oligomerization, an acylation, a hydrocracking, a metathesis, a copolymerization, an isomerization, a carbonylation, a hydroformylation, a dehalogenation, a dehydration, a disproportionation, a transalkylation, and combinations thereof. In one embodiment, the hydrocarbon conversion is alkylation of paraffins with olefins. In another embodiment, the hydrocarbon conversion is alkylation of aromatics. Examples of ionic liquid catalysts and their use for alkylation of paraffins with olefins are taught, for example, in U.S. Pat. Nos. 7,432,408 and 7,432,409, 7,285,698, and U.S. patent application Ser. No. 12/184,069, filed Jul. 31, 2008. In one embodiment, the acidic ionic liquid is a composite ionic liquid catalyst, wherein the cations come from a hydrohalide of an alkyl-containing amine or pyridine, and the anions are composite coordinate anions coming from two or more metal compounds. In another embodiment the conversion of a hydrocarbon is alkylation of paraffins, alkylation of aromatics, or combinations thereof.

The most common acidic ionic liquids are those prepared from organic-based cations and inorganic or organic anions. Ionic liquid catalysts are used in a wide variety of reactions, including Friedel-Crafts reactions.

The acidic ionic liquid is composed of at least two components which form a complex. The acidic ionic liquid comprises a first component and a second component. The first component of the acidic ionic liquid will typically comprise a Lewis acid compound selected from components such as Lewis acid compounds of Group 13 metals, including aluminum halides, alkyl aluminum dihalides, gallium halide, and alkyl gallium halide (see the Periodic Table, which defines the elements that are Group 13 metals). Other Lewis acid compounds besides those of Group 13 metals may also be used. In one embodiment the first component is aluminum halide or alkyl aluminum dihalide. For example, aluminum trichloride ($AlCl_3$) may be used as the first component for preparing the ionic liquid catalyst. In one embodiment, the alkyl aluminum dihalides that can be used can have the general formula $Al_2X_4R_2$, where each X represents a halogen, selected for example from chlorine and bromine, each R represents a hydrocarbyl group comprising 1 to 12 atoms of carbon, aromatic or aliphatic, with a branched or a linear chain. Examples of alkyl aluminum dihalides include dichloromethylaluminum, dibromomethylaluminum, dichloroethylaluminum, dibromoethylaluminum, dichloro n-hexylaluminum, dichloroisobutylaluminum, either used separately or combined.

The second component making up the acidic ionic liquid is an organic salt or mixture of salts. These salts may be characterized by the general formula $Q^+A^-$, wherein $Q^+$ is an ammonium, phosphonium, boronium, oxonium, iodonium, or sulfonium cation and $A^-$ is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $Al_2Cl_7^-$, $Al_3Cl_{10}^-$, $GaCl_4^-$, $Ga_2Cl_7^-$, $Ga_3Cl_{10}^-$, $AsF_6^-$, $TaF_6^-$, $CuCl_2^-$, $FeCl_3^-$, $AlBr_4^-$, $Al_2Br_7^-$, $Al_3Br_{10}^-$, $SO_3CF_3^-$, and 3-sulfurtrioxyphenyl. In one embodiment the second component is selected from those having quaternary ammonium halides containing one or more alkyl moieties having from about 1 to about 9 carbon atoms, such as, for example, trimethylammonium hydrochloride, methyltributylammonium, 1-butyl pyridinium, or alkyl substituted imidazolium halides, such as for example, 1-ethyl-3-methylimidazolium chloride.

In one embodiment, the acidic ionic liquid comprises a monovalent cation selected from the group consisting of a pyridinium ion, an imidazolium ion, a pyridazinium ion, a pyrazolium ion, an imidazolinium ion, a imidazolidinium ion, an ammonium ion, a phosphonium ion, and mixtures thereof. Examples of possible cations ($Q^+$) include a butylethylimidazolium cation [beim], a butylmethylimidazolium cation [bmim], butyldimethylimidazolium cation [bmmim], decaethylimidazolium cation [dceim], a decamethylimidazolium cation [dcmim], a diethylimidazolium cation [eeim], dimethylimidazolium cation [mmim], an ethyl-2,4-dimethylimidazolium cation [e-2,4-mmim], an ethyldimethylimidazolium cation [emmim], an ethylimidazolium cation [eim], an ethylmethylimidazolium [emim] cation, an ethylpropylimidazolium cation [epim], an ethoxyethylmethylimidazolium cation [etO-emim], an ethoxydimethylimidazolium cation [etO-mmim], a hexadecylmethylimidazolium cation [hexadmim], a heptylmethylimidazolium cation [hpmim], a hexaethylimidazolium cation [hxeim], a hexamethylimidazolium cation [hxmim], a hexadimethylimidazolium cation [hxmmim], a methoxyethylmethylimidazolium cation [meO-emim], a methoxypropylmethylimidazolium cation [meO-prmim], a methylimidazolium cation [mim], dimethylimidazolium cation [mmim], a methylnonylimidazolium cation [mnim], a methylpropylimidazolium cation [mpim], an octadecylmethylimidazolium cation [octadmim], a hydroxylethylmethylimidazolium cation [OH-emim], a hydroxyloctylmethylimidazolium cation [OH-omim], a hydroxylpropylmethylimidazolium cation [OH-prmim], an octylmethylimidazolium cation [omim], an octyldimethylimidazolium cation [ommim], a phenylethylmethylimidazolium cation [ph-emim], a phenylmethylimidazolium cation [ph-mim], a phenyldimethylimidazolium cation [ph-mmim], a pentylmethylimidazolium cation [pnmim], a propylmethylimidazolium cation [prmim], a 1-butyl-2-methylpyridinium cation[1-b-2-mpy], 1-butyl-3-methylpyridinium cation[1-b-3-mpy], a butylmethylpyridinium [bmpy] cation, a 1-butyl-4-dimethylacetylpyridinium cation [1-b-4-DMApy], a 1-butyl-4-methylpyridinium cation[1-b-4-mpy], a 1-ethyl-2-methylpyridinium cation[1-e-2-mpy], a 1-ethyl-3-methylpyridinium cation[1-e-3-mpy], a 1-ethyl-4-dimethylacetylpyridinium cation[1-e-4-DMApy], a 1-ethyl-4-methylpyridinium cation[1-e-4-mpy], a 1-hexyl-4dimethylacetylpyridinium cation[1-hx-4-DMApy], a 1-hexyl-4-methylpyridinium cation[1-hx-4-mpy], a 1-octyl-3-methylpyridinium cation[1-o-3-mpy], a 1-octyl-4-methylpyridinium cation[1-o-4-mpy], a 1-propyl-3-methylpyridinium cation[1-pr-3-mpy], a 1-propyl-4-methylpyridinium cation[1-pr-4-mpy], a butylpyridinium cation [bpy], an ethylpyridinium cation [epy], a heptylpyridinium cation [hppy], a hexylpyridinium cation [hxpy], a hydroxypropylpyridinium cation [OH-prpy], an octylpyridinium cation [opy], a pentylpyridinium cation [pnpy], a propylpyridinium cation [prpy], a butylmethylpyrrolidinium cation [bmpyr], a butylpyrrolidinium cation [bpyr], a hexylmethylpyrrolidinium cation [hxmpyr], a hexylpyrrolidinium cation [hxpyr], an octylmethylpyrrolidinium cation [ompyr], an octylpyrrolidinium cation [opyr], a propylmethylpyrrolidinium cation [prmpyr], a butylammonium cation [b-N], a tributylammonium cation [bbb-N], a tetrabutylammonium cation [bbbb-N], a butylethyldimethylammonium cation [bemm-N], a butyltrimethylammonium cation [bmmm-N], a N,N,N-trimethylethanolammonium cation [choline], an ethylammonium cation [e-N], a diethylammonium cation [ee-N], a tetraethylammonium cation [eeee-N], a tetraheptylammonium cation [hphphphp-N], a tetrahexylammonium cation [hxhxhxhx-N], a methylammonium cation [m-N], a dimethylammonium cation [mm-N], a tetramethylammonium cation [mmmm-N], an ammonium cation [N], a butyldimethylethanolammonium cation [OHe-bmm-N], a dimethylethanolammonium cation [OHe-mm-N], an ethanolammonium cation [OHe—N], an ethyldimethylethanolammonium cation [OHe-emm-N], a tetrapentylammonium cation [pnpnpnpn-N], a tetrapropylammonium cation [prprprpr-N], a tetrabutylphosphonium cation [bbbb-P], a tributyloctylphosphonium cation [bbbo-P], or combinations thereof.

In one embodiment, the second component is selected from those having quaternary phosphonium halides containing one or more alkyl moieties having from 1 to 12 carbon atoms, such as, for example, trialkyphosphonium hydrochloride, tetraalkylphosphonium chlorides, and methyltrialkyphosphonium halide.

In one embodiment, the acidic ionic liquid comprises an unsubstituted or partly alkylated ammonium ion.

In one embodiment, the acidic ionic liquid is chloroaluminate or a bromoaluminate. In one embodiment the acidic ionic liquid is a quaternary ammonium chloroaluminate ionic liquid having the general formula RR'R"NH$^+$ Al$_2$Cl$_7^-$, wherein R, R', and R" are alkyl groups containing 1 to 12 carbons. Examples of quaternary ammonium chloroaluminate ionic liquids are an N-alkyl-pyridinium chloroaluminate, an N-alkyl-alkylpyridinium chloroaluminate, a pyridinium hydrogen chloroaluminate, an alkyl pyridinium hydrogen chloroaluminate, a di alkyl-imidazolium chloroaluminate, a tetra-alkyl-ammonium chloroaluminate, a tri-alkyl-ammonium hydrogen chloroaluminate, or a mixture thereof.

The presence of the first component should give the acidic ionic liquid a Lewis or Franklin acidic character. Generally, the greater the mole ratio of the first component to the second component, the greater is the acidity of the acidic ionic liquid.

For example, a typical reaction mixture to prepare n-butyl pyridinium chloroaluminate ionic liquid is shown below:

In one embodiment, the acidic ionic liquid is used as a catalyst for a hydrocarbon conversion and the hydrocarbon conversion utilizes a co-catalyst to provide enhanced or improved catalytic activity. In one embodiment, the hydrocarbon conversion is alkylating a mixture of one or more C$_4$-C$_7$ isoparaffins and one or more C$_2$-C$_6$ olefins in a presence of an acidic ionic liquid and an alkyl halide or a hydrogen halide to produce an alkylate gasoline blending component. The alkyl halide or the hydrogen halide can be co-catalysts for the hydrocarbon conversion. A co-catalyst can comprise, for example, anhydrous HCl or organic chloride (see, e.g., U.S. Pat. No. 7,495,144 to Elomari, and U.S. Pat. No. 7,531,707 to Harris et al.) When organic chloride is used as the co-catalyst with the acidic ionic liquid, HCl may be formed in situ in the apparatus either during the hydrocarbon conversion process or during post-processing of the output of the hydrocarbon conversion. In one embodiment, the hydrocarbon conversion is conducted in the presence of a hydrogen halide, e.g., HCl.

The alkyl halides that may be used include alkyl bromides, alkyl chlorides and alkyl iodides. A variety of alkyl halides may be used, but alkyl halide derivatives of the hydrocarbons that comprise the feed streams to the hydrocarbon conversion (e.g., isoparaffins or the olefins for alkylating) can be preferable. Such alkyl halides include but are not limited to iospentyl halides, isobutyl halides, tertiary butyl halides, n-butyl halides, propyl halides and ethyl halides. Alkyl chloride versions of these alkyl halides are preferable when chloroaluminate ionic liquids are used. Other alkyl chlorides or alkyl halides having from 1 to 8 carbon atoms may be also used. The alkyl halides may be used alone or in combination.

When used, the alkyl halide or hydrogen halide are used in catalytic amounts. In one embodiment, the amounts of the alkyl halides or hydrogen halide should be kept at low concentrations and not exceed the molar concentration of the AlCl$_3$ in the acidic ionic liquid. For example, the amounts of the alkyl halides or hydrogen halide used may range from 0.05 mol %-100 mol % of the Lewis acid AlCl$_3$ in the acidic ionic liquid in order to keep the acidity of the acidic ionic liquid catalyst at the desired performing capacity.

Spent Acidic Ionic Liquid:

Spent acidic ionic liquid can be made by using the acidic ionic liquid to perform the hydrocarbon conversion. Over time, the acidic ionic liquid accumulates impurities and becomes less active and selective for performing the desired hydrocarbon conversion. One of the impurities that accumulates in the acidic ionic liquid is conjunct polymer. The conjunct polymer deactivates the acidic ionic liquid by weakening the acid strength of the acidic ionic liquid. Complexation of the conjunct polymer with the acidic ionic liquid can deplete the concentration of the Lewis acid in the acidic ionic liquid. As more conjunct polymers accumulate in the acidic ionic liquid the acidic ionic liquid becomes weaker for performing the desired catalysis. In one embodiment, the spent acidic ionic liquid comprises greater than 3 wt % of the conjunct polymer. For example, the spent acidic ionic liquid can have from greater than 3 wt % to 30 wt % conjunct polymer.

The spent acidic ionic liquid can also comprise corrosion metals. The corrosion metals can leach from the metal materials that the acidic ionic liquid contacts. Examples of metal materials used for vessels and equipment handling acidic ionic liquids are steel, titanium, nickel-copper alloys, and nickel-based super alloys. Examples of some of these metal materials include Inconel® alloys, Incoloy® alloys, Monel® 400 alloy, and Hastelloy® alloys. The compositions of some of these specific alloys are summarized in Table 1. Inconel® and Incoloy® are trademarks of Special Metals Corporation.

TABLE 1

Nickel-Copper Alloy Chemical Composition Ranges (all values in weight percent):

| Alloy | UNS # | Ni | Cu | Fe | Mn | Si | S | C |
|---|---|---|---|---|---|---|---|---|
| Monel® 400 | N04400 | 63.0 min | 28-34 | 2.50 max | 2.0 max | 0.024 max | 0.50 max | 0.30 max |

Monel® is a trademark of Special Metals.

TABLE 2

Nickel Based Super Alloy Elemental Composition Ranges (all values in weight percent):

| Hastelloy ® | UNS # | Ni | Cr | Mo | Fe | W | Co |
|---|---|---|---|---|---|---|---|
| C-276 | N10276 | Balance | 14.5-16.5 | 15-17 | 4-7 | 3-4.5 | 2.5 max |
| C-22 | N06022 | Balance | 20-22.5 | 12.5-14.5 | 2-6 | 2.5-3.5 | 2.5 max |
| B2 | N10665 | Balance | 1.0 max | 26-30 | 2.0 max | — | 1.0 max |

| Hastelloy ® | UNS # | Mn | C | P | Si | S | V |
|---|---|---|---|---|---|---|---|
| C-276 | N10276 | 1.0 max | 0.01 max | 0.04 max | 0.08 max | 0.03 max | 0.35 max |
| C-22 | N06022 | 0.50 max | 0.01 max | 0.02 max | 0.08 max | 0.02 max | 0.35 max |
| B2 | N10665 | 1.0 max | 0.02 max | 0.04 max | 0.10 max | 0.03 max | — |

Hastelloy ® is a trademark of Haynes International, Inc.

In one embodiment, the spent ionic liquid comprises from 100 wppm to 50,000 wppm corrosion metals. In one embodiment, the spent ionic liquid comprises less than 10,000 wppm corrosion metals. In one embodiment, the spent ionic liquid comprises from 10 to 2,500 wppm nickel, wherein the nickel is a corrosion metal.

In one embodiment, the spent acidic ionic liquid catalyst comprises a metal halide. Without being bound by theory, it is possible that a homogeneous metal halide complex forms in situ in the spent acidic ionic liquid catalyst, and that this complex functions as a homogeneous hydrogenation catalyst. In one embodiment, the homogeneous metal halide complex comprises nickel.

Regenerated Acidic Ionic Liquid:

After the contacting, the content of the conjunct polymer in the spent acidic ionic liquid is decreased enough such that the acidic ionic liquid is regenerated. In one embodiment, the content of the conjunct polymer in the regenerated acidic ionic liquid is 30 wt % to 100 wt % of the amount of the conjunct polymer in the spent acidic ionic liquid. In one embodiment, the conjunct polymer in the regenerated acidic ionic liquid is decreased by at least 50 wt %. In one embodiment the regenerated acidic ionic liquid comprises from 0 to 5 wt % conjunct polymer. In one embodiment, the regenerated acidic ionic liquid comprises less than 1.5 wt % of the conjunct polymer.

Feeds for the Hydrocarbon Conversion:

In one embodiment, the feed to the hydrocarbon conversion comprises at least one olefin and at least one isoparaffin. For example the feed can comprise a mixture of at least one mostly linear olefin from $C_2$ to about $C_{30}$. In another embodiment, the feed can comprise at least 50% of a single alpha olefin species. In one embodiment, the olefin feed comprises at least one isomerized olefin.

In one embodiment, the feed to an alkylation reactor comprises one or more $C_4$-$C_7$ isoparaffins and one or more $C_2$-$C_6$ olefins, and the process produces an alkylate gasoline blending component.

In one embodiment, the feed to the hydrocarbon conversion comprises isobutane. Isopentanes, isohexanes, isoheptanes, and other higher isoparaffins up to about $C_{30}$ are also useable in the process and apparatuses disclosed herein. Mixtures of light isoparaffins can also be used in the present invention. Mixtures such as $C_3$-$C_4$, $C_3$-$C_5$, or $C_4$-$C_5$ isoparaffins can also be used and may be advantaged because of reduced separation costs. The feed to the hydrocarbon conversion can also contain diluents such as normal paraffins. This can be a cost savings by reducing the cost of separating isoparaffins from close boiling paraffins. In one embodiment, the normal paraffins will tend to be unreactive diluents in the hydrocarbon conversion.

Reuse of a Previously Used Hydrogenation Vessel:

In one embodiment, a vessel previously containing a solid hydrogenation catalyst is emptied of the solid hydrogenation catalyst and reused for the contacting. Even without the solid hydrogenation catalyst in the vessel, the hydrogenation is effective for regenerating the spent acidic ionic liquid catalyst.

Apparatus:

In one embodiment, we provide an apparatus that is used for performing the processes disclosed herein. The apparatus can comprise a vessel comprising an inlet for introducing the hydrogen, a second inlet for introducing the spent acidic ionic liquid, equipment that provides mixing of the hydrogen and the spent acidic ionic liquid, a vent, no parts used for separately adding a hydrogenation catalyst, and an outlet for removing the regenerated acidic ionic liquid. In one embodiment, the vessel is a stirred tank reactor where efficient mixing of hydrogen and the spent acidic ionic liquid catalyst is achieved. In one embodiment, the vessel can comprise an internal particulate filter, having no hydrogenation activity, which provides some or all of the mixing and can be used for improving dispersion and/or adsorbing any contaminants from the spent acidic ionic liquid. Examples of vessels that could use an internal particulate filter in this manner could include flow-through open tubes, plug-flow reactors, or bubble columns. One example of a suitable particulate filter is a Crystaphase CatTrap® internal particulate filter. In one embodiment, the internal particulate filter is a reticulated ceramic which comes in large discs (1.5" to 2" diameter). These discs can have the ability to filter and store particles inside the discs. Because the large external pathways in the discs stay open, there is no pressure drop build up as the material filters.

EXAMPLES

Example 1: Spent Acidic Ionic Liquid Catalyst

A sample of spent acidic ionic liquid catalyst was obtained from an alkylation process unit producing alkylate gasoline blending component. The spent acidic ionic liquid catalyst comprised n-butyl pyridinium chloroaluminate ionic liquid, conjunct polymer, and additional elements. The additional elements included dissolved metals, some as metal halides. The additional elements were dissolved and were not a colloidal suspension of solids. The dissolved metals were formed by the corrosion of Monel piping in the alkylation process unit. This sample of spent acidic ionic liquid catalyst had the following properties:

TABLE 3

| Spent Acidic Ionic Liquid from Alkylation Reactor | |
| --- | --- |
| Conjunct Polymer Content, wt % | 4.10 |
| Elemental Analyses, wppm | |
| Chromium | 298 |
| Copper | 3520 |
| Iron | 2060 |
| Manganese | 158 |
| Nickel | 1820 |
| Sulfur | 255 |

The method used to measure the conjunct polymer content was vibrational infrared spectroscopy, as described in US Patent Publication No. US20120296145A1.

To perform the elemental analyses the samples were prepared using a Milestone Ethos Plus™ closed vessel microwave digestion system according to ASTM D4309-12, "Standard Practice for Sample Digestion Using Closed Vessel Microwave Heating Technique for the Determination of Total Metals in Water". The digested solutions were then analyzed by inductively coupled plasma-atomic emission spectrometry (ICP-AES) according to ASTM D7260-12, "Standard Practice for Optimization, Calibration, and Validation of Inductively Coupled Plasma-Atomic Emission Spectrometry (ICP-AES) for Elemental Analysis of Petroleum Products and Lubricants".

The spent acidic ionic liquid catalyst sample was examined under a scanning electron microscope (SEM) using a Mylar sample cell that kept the spent acidic ionic liquid sample in an anhydrous atmosphere. Using a back scattering technique, the presence of particles containing corrosion metal elements was searched and no solid metal particles containing heavy metals (Ni, Fe, and Cu) were observed.

Figure 1:
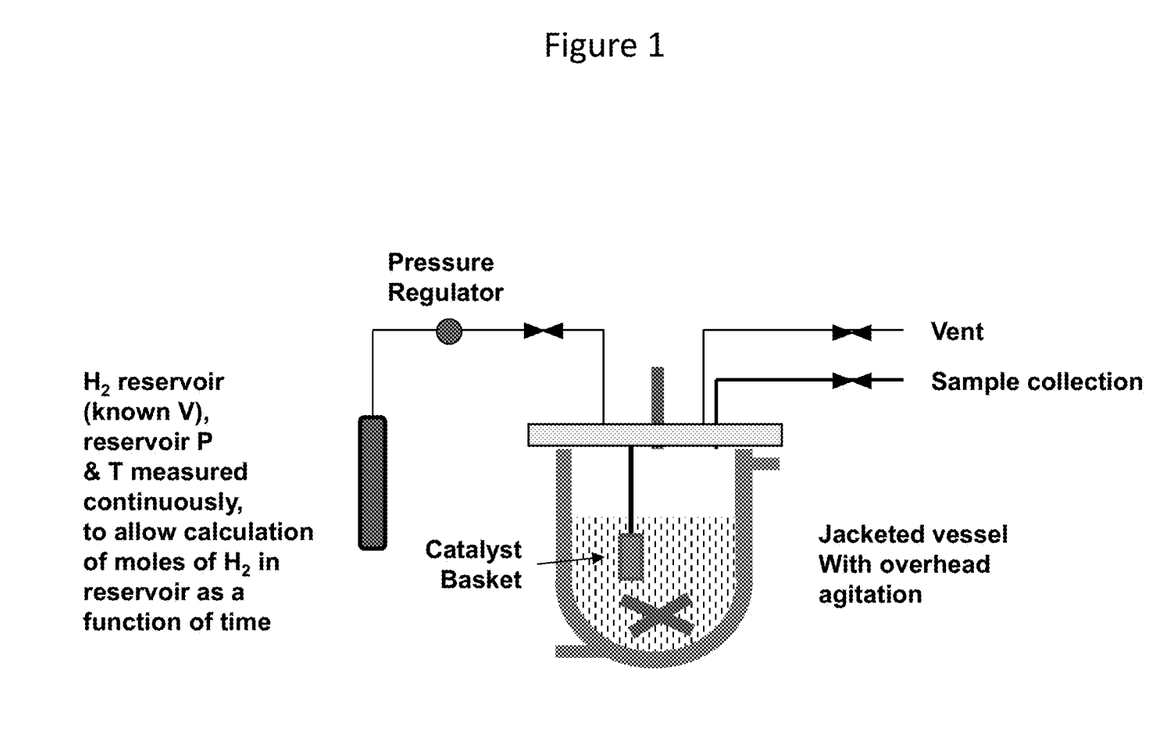
FIG. 1 is a schematic diagram of the experimental apparatus used in Examples 2 and 4-7 in this disclosure.

Example 2: Hydro-Regeneration in the Absence of Added Catalyst and with Vessel Drying and Hydrogen Pre-Treatment An empty 1.2 liter jacketed HASTELLOY® C-22 vessel, equipped with a HASTELLOY C-22 temperature sensor, HASTELLOY C-22 catalyst basket, and HASTELLOY C-22 gassing agitator, were heated to 176.7° C. (350° F.) under a flow of 190 cc/min. of nitrogen and held at that temperature for 15 hours to dry the vessel. HASTELLOY is a registered trademark of Haynes International, Inc. The apparatus used for this example is shown in FIG. 1. The flow of nitrogen was stopped, and hydrogen gas was introduced into the vessel at 190 cc/min. The vessel was subsequently pressurized with hydrogen at 400 psig (2860 kpa) and held at this same temperature and pressure for seven hours. The vessel was then cooled to room temperature, depressurized, and hydrogen was purged from the vessel by pressurizing the vessel with nitrogen to 400 psig (2860 kpa), depressurizing, and repeating this pressurization/depressurization sequence twice.

510 g of the spent acidic ionic liquid catalyst described in Example 1 was charged to the vessel by nitrogen pressure transfer from a glass bottle. No catalyst was added to the catalyst basket. The vessel was purged with nitrogen by pressuring the vessel with nitrogen to 400 psig (2860 kpa), depressurizing, and repeating this pressurization/depressurization sequence twice. About 50 psig (445 kpa) of nitrogen was applied, and the vessel was heated to 180° C. (356° F.) over two hours while agitating at 400 rpm. When the target 180° C. (356° F.) temperature was reached, a sample was taken from the vessel and analyzed for conjunct polymer content. The conjunct polymer content was 4.26 wt %, which was close to the 4.10 wt % in the spent acidic ionic liquid catalyst that was analyzed prior to charging it to the vessel. The agitation was stopped, and hydrogen was exchanged for the nitrogen in the headspace of the vessel by depressurizing the vessel, pressurizing with hydrogen to 400 psig (2860 kpa), depressurizing, and repeating the pressurization/depressurization cycle twice. The vessel was then pressurized to a 400 psig (2860 kpa) reaction pressure with hydrogen. The agitator was started at 700 rpm to obtain a well-defined time for the start of reaction. Reaction progress was monitored two ways: (a) by measuring the hydrogen consumption, calculated from the pressure change of the reservoir feeding the vessel, and (b) by analyzing samples taken directly from the vessel using vibrational infrared spectroscopy.

Figure 2:
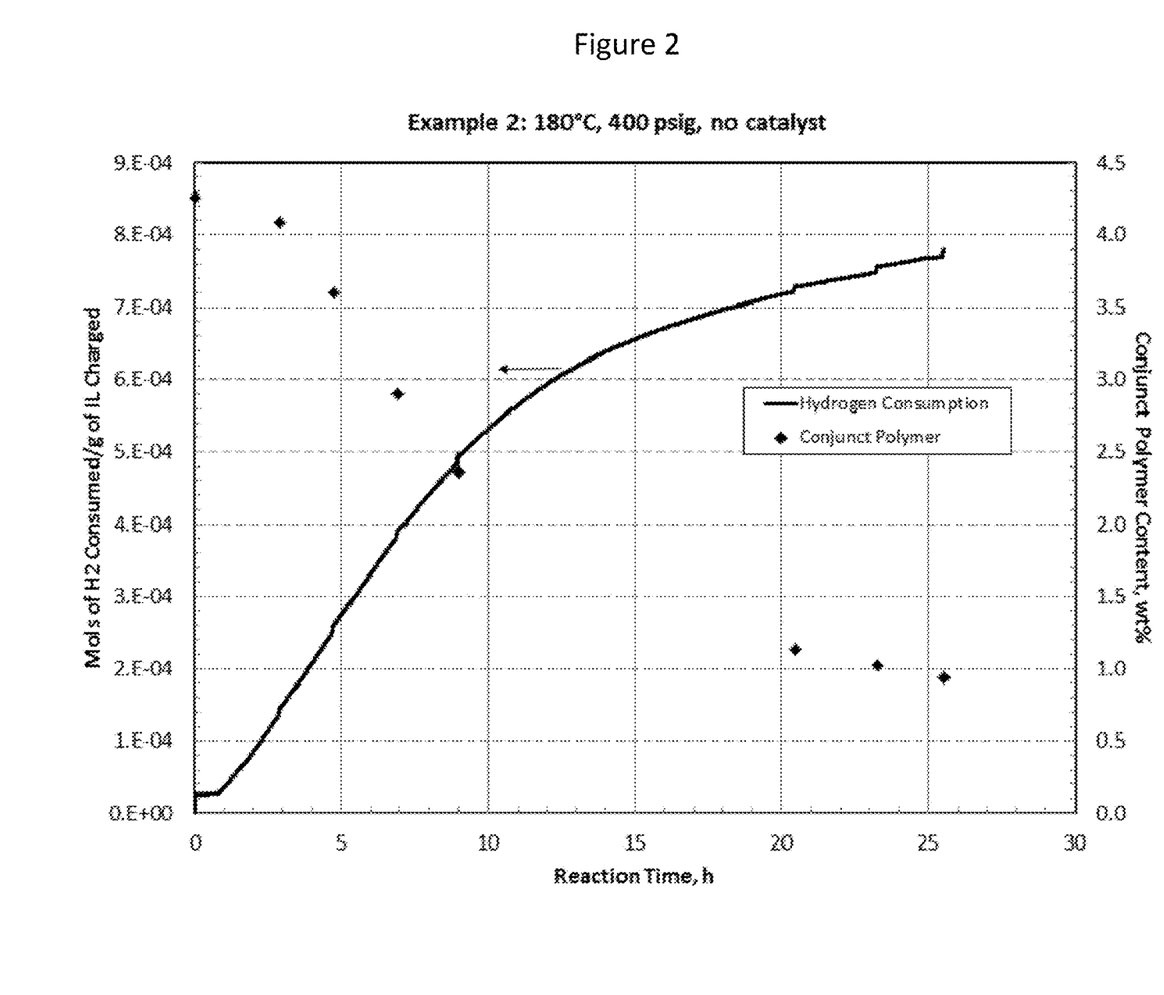
FIG. 2 is a graph of the moles of hydrogen consumed/g of ionic liquid, and conjunct polymer content, plotted vs. the reaction time from the Example 2 in this disclosure.

The data from this run is shown in FIG. 2. The hydrogen consumption profile flattened about 20 hours after the start of reaction, and the conjunct polymer content decreased from 4.26 wt % to about 1 wt % over the same time period. The correlation of the hydrogen consumption profile with the decrease in conjunct polymer content showed that the decrease in the conjunct polymer content occurred due to a combination of hydrogenation and hydrocracking. Hydrogenations are catalyzed by metals (see page 4) whereas hydrocracking typically requires a bifunctional metal catalyst comprising a hydrogenation function and an acidic function, typically from an acidic support or perhaps an acidic solvent. One novel and remarkable feature of this example was the occurrence of hydrogenation and hydrocracking in the complete absence of any added hydrocracking or hydrogenation catalyst. In theory, the catalytic hydrogenation activity can be attributed in part to the dissolved corrosion metals, which originated from either corrosion of Monel piping in the alkylation unit and which were present in a concentration exceeding 1000 ppm (see Example 1) or from corrosion of the Hastelloy vessel wall and inserts.

Example 3: Lab-Prepared Spent Acidic Ionic Liquid

A lab-prepared spent acidic ionic liquid catalyst comprising n-butyl pyridinium chloroaluminate ionic liquid, conjunct polymer, and without significant amounts of additional elements, was prepared as follows. 272 g of t-butyl chloride was added to a glass flask containing about 1358 g fresh n-butyl pyridinium chloroaluminate ionic liquid and 100 ml n-heptane. The mixture was stirred in the glass flask while immersed in an ice bath for 1.5 hours, then removed from the ice bath and stirred for an additional hour. The as-prepared reaction product in the glass flask had 6.9 wt % conjunct polymer, and it was diluted with fresh n-butyl pyridinium chloroaluminate ionic liquid to a level of 4.4 wt % conjunct polymer. This sample of lab-prepared spent acidic ionic liquid catalyst had the following properties:

TABLE 4

| Lab-Prepared Spent Acidic Ionic Liquid | |
| --- | --- |
| Conjunct Polymer Content, wt % | 4.4 |
| Elemental Analyses, wppm | |
| Chromium | <2.9 |
| Iron | <23 |
| Molybdenum | <5.7 |
| Nickel | <2.9 |
| Sulfur | <29 |

One key feature of this lab-prepared conjunct polymer was its low metal content (<10 wppm), which was in sharp contrast to the spent acidic ionic liquid from the alkylation plant (Table 3). This lab-prepared conjunct polymer with a low metal content was well suited to investigate the impact of dissolved metals on decreasing the content of the conjunct polymer, or conjunct polymer removal.

Example 4: Hydro-Regeneration in the Absence of Added Catalyst and without Vessel Drying and Hydrogen Pre-Treatment The empty 1.2 liter jacketed HASTELLOY® C-22 vessel described in Example 2 was charged with 510 g sample of the lab-prepared spent acidic ionic liquid described in Example 3. No hydrogenation catalyst was added to the catalyst basket. In this example, vessel drying and hydrogen pre-treatment were not carried out. The lab-prepared spent acidic ionic liquid in the vessel was heated to 180° C. (356° F.) over 1.8 hours, the vessel headspace was exchanged with hydrogen, and the reaction started as described for Example 2.

Figure 3:
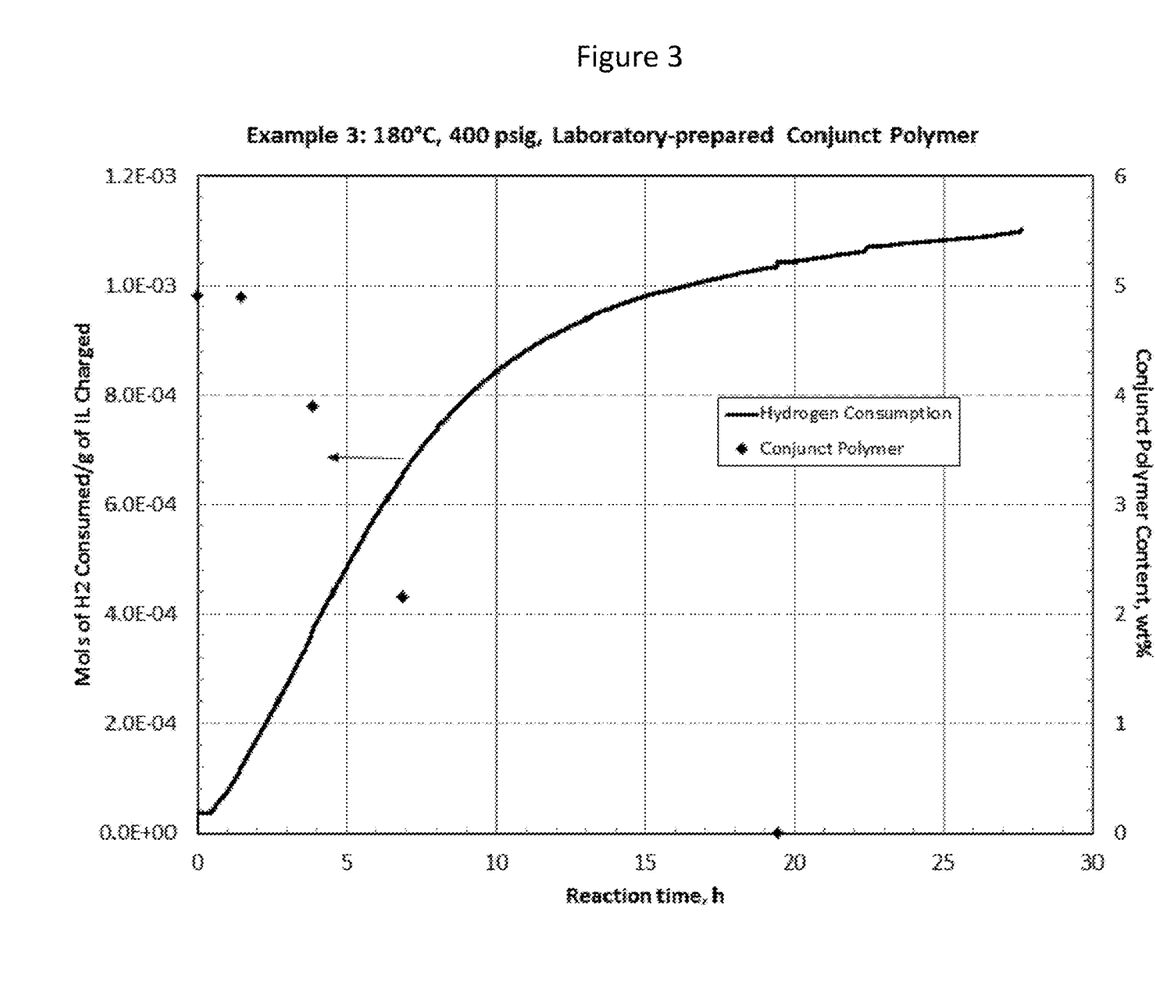
FIG. 3 is a graph of the moles of hydrogen consumed/g of ionic liquid, and conjunct polymer content, plotted vs. the reaction time from the Example 3 in this disclosure

The data from this experiment is shown in FIG. 3. Hydrogen consumption was again correlated with conjunct polymer decrease, similar to the findings in Example 2. The conjunct polymer content decreased from 4.4 wt % to about 0 wt % (less than detectable) in less than 20 hours of reaction time. No solids formation occurred in the vessel. This example demonstrated that the hydro-regeneration of the spent acidic ionic liquid catalyst was conducted in the absence of an added hydrogenation catalyst, and even without drying or hydrogen pre-treatment. No solids were added or formed in the vessel used for the contacting.

More significantly, the decrease in the content of conjunct polymer by hydrogenation/hydrocracking occurred with a much lower level of corrosion metals present in the feed. Despite the occurrence of some corrosion in the vessel (as evidenced, for example, by the increase in nickel from 33 wppm at the reaction start to 376 wppm at the reaction end), the conjunct polymer removal occurred even though the corrosion metals content was more than an order of magnitude lower than in Example 1. The impact of corrosion metals on conjunct polymer removal is evidently weak,

TABLE 5

Metal Leaching in Lab-Prepared Spent Acidic Ionic Liquid Catalyst

|  | Freshly Prepared | After Heating, Before Hydrogen Introduction | After 22.4 Hours Contact with Hydrogen |
|---|---|---|---|
| Conjunct Polymer Content, wt % | 4.4 | 4.9 | 0 |
| Elemental Analyses, wppm | | | |
| Chromium | <2.9 | 18.4 | 154.0 |
| Iron | <23 | 44.8 | 94.5 |
| Molybdenum | <5.7 | 17.6 | 64.5 |
| Nickel | <2.9 | 33.3 | 376.0 |
| Sulfur | <29 | <25 | <21 |

Figure 4:
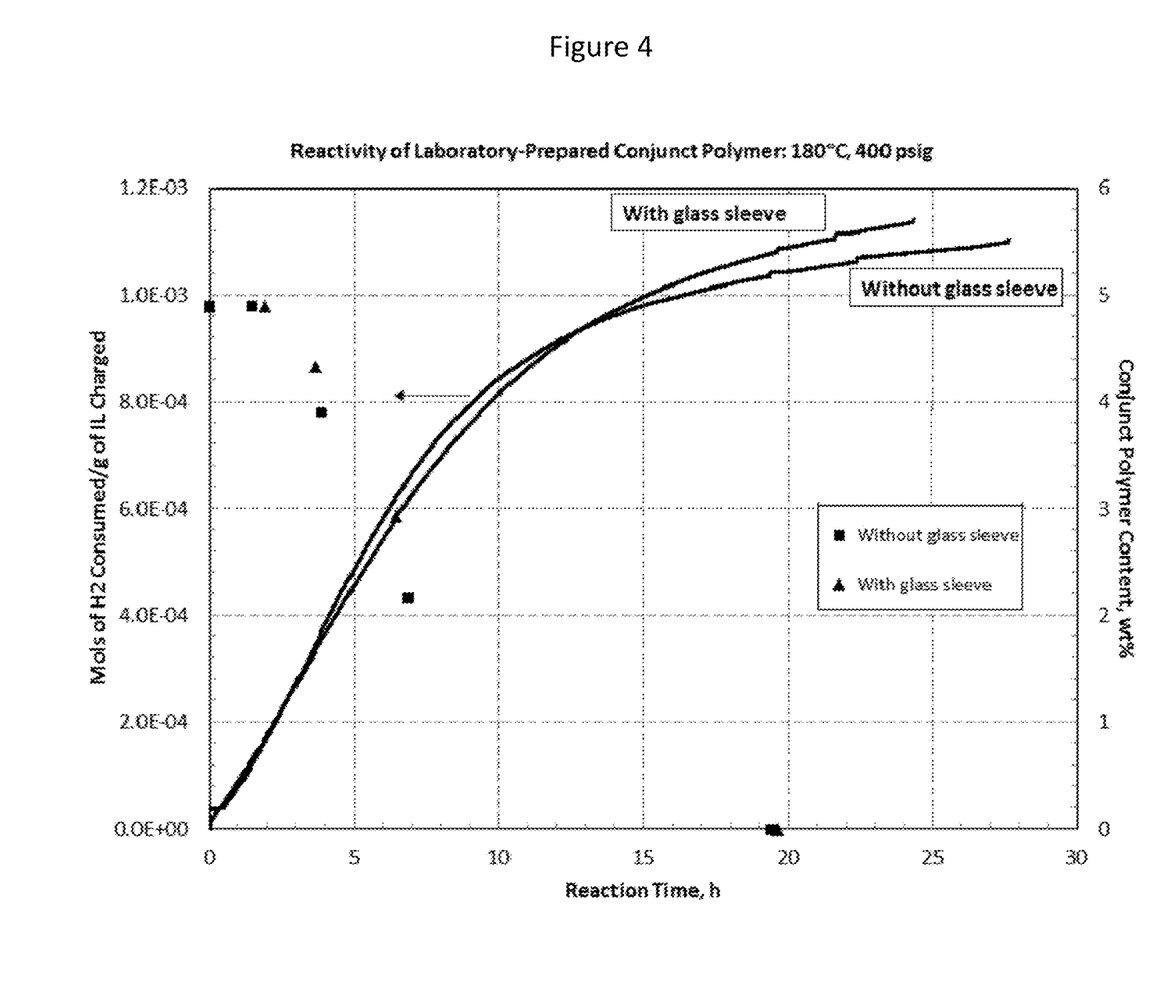
FIG. 4 is a graph of the moles of hydrogen consumed/g of ionic liquid, and conjunct polymer content, plotted vs. the reaction time from the two sets of experiments described in Example 5 of this disclosure.

Example 5: Hydro-Regeneration in the Absence of Added Catalyst, without Vessel Drying and Hydrogen Pre-Treatment, and with Minimal Exposure to Metal Surfaces The experiment described in Example 4 was repeated, but with a glass sleeve placed in the vessel to minimize exposure of the spent acidic ionic liquid catalyst to metal surfaces. The catalyst basket was removed before starting this experiment, and a pitched-blade impeller with a solid shaft was used instead of the hollow shaft gassing agitator used in Examples 1 and 3. The aforementioned changes decreased the metal surface area exposed to the ionic liquid by 85%, thus decreasing exposure of metal surfaces to the acidic ionic liquid significantly. As shown in FIG. 4, the impact of significantly smaller metal exposure to the acidic ionic liquid did not impact the rate of decrease in content of the conjunct polymer significantly. As expected, the dissolved metals content in the reaction mixture was much lower due to the smaller metal exposure; for example, the nickel content ranged from 17 to 140 wppm over the length of the reaction vs. 33-376 wppm in Example 4.

This example thus indicated that a lower metals content in the acidic ionic liquid at the start of reaction had no significant impact on the rate of decrease of the conjunct polymer content for the same acidic ionic liquid. It indicated further that the impact of corrosion metals concentration in the acidic ionic liquid on the rate of decrease of the conjunct polymer content was weak, or negligible.

Example 6: Composition of Headspace Gas

Another regeneration experiment was conducted in a manner similar to that described in Example 4, but at a 230° C. (446° F.) reaction temperature. The headspace gas composition was analyzed using an on-line gas chromatograph (GC), connected to the same line as used for the vent.

TABLE 6

GC Analysis of Headspace Gas

| Component | Area % |
|---|---|
| Methane | 4.92 |
| Ethane | 9.24 |
| Propane | 30.22 |
| i-Butane | 29.06 |
| n-Butane | 17.36 |
| i-Pentane | 6.71 |
| n-Pentane | 1.83 |

The GC analysis of the headspace gas revealed that only alkanes were formed. While not being bound by theory, the findings that the headspace gas comprised only alkanes and that no olefins were formed was consistent with the expected product distribution obtained by catalytic hydrocracking. In catalytic hydrocracking, initially formed olefins due to cracking are thought to be hydrogenated to give paraffins.

Even at the highest temperature used (namely, 230° C.), no light olefinic components (typically formed in thermal cracking) were detected.

Example 7: Impact of Pressure on Conjunct Polymer Decrease Rate

Figure 5:
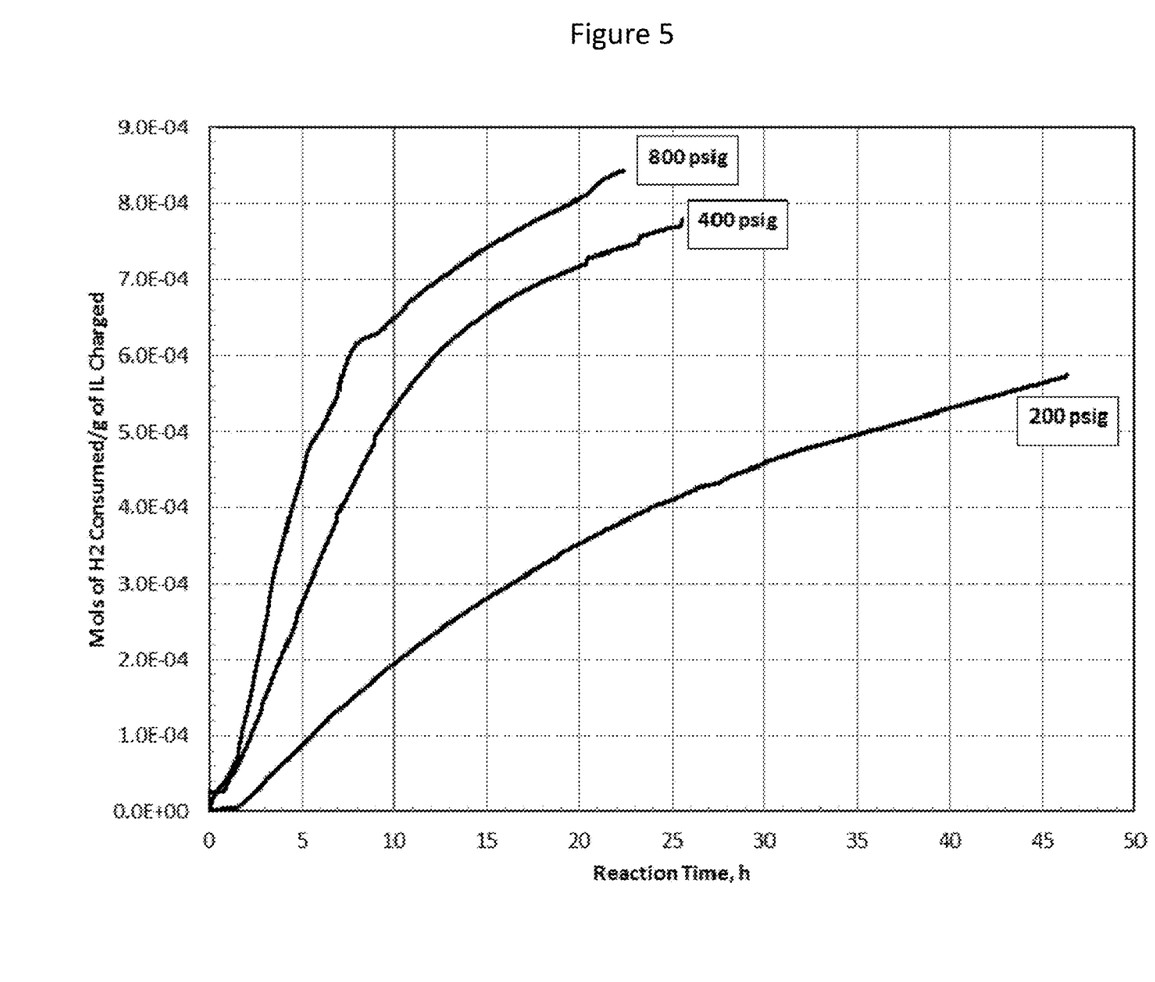
FIG. 5 is a graph of the moles of hydrogen consumed/g of ionic liquid vs. the reaction time in the three sets of experiments described in Example 7 of this disclosure.
Figure 6:
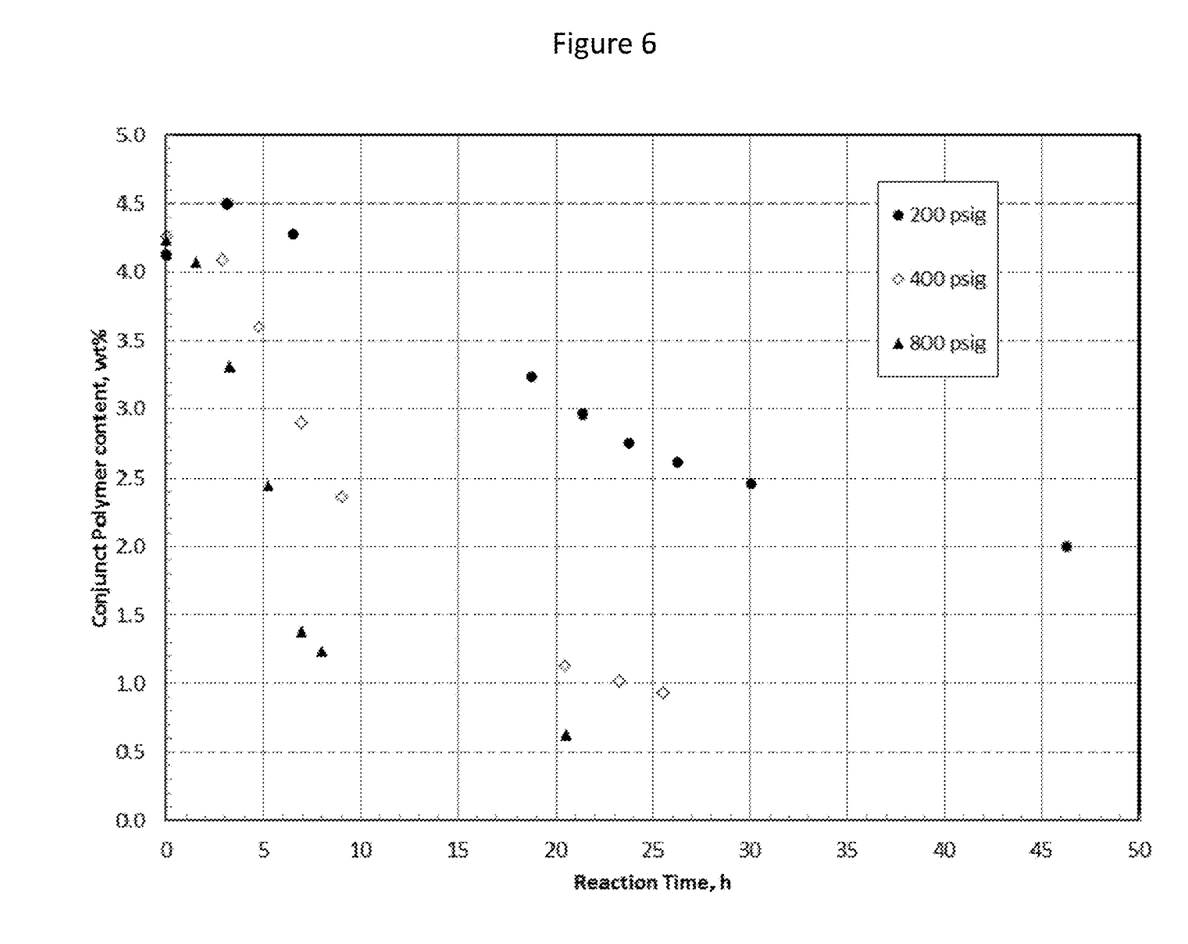
FIG. 6 is a graph of the wt % conjunct polymer content vs. the reaction time in the three sets of experiments described in Example 7 of this disclosure.

The experiment described in Example 2 was repeated at two other operating pressures of 200 psig, and 800 psig. The results of these experiments were compared to results at 400 psig (Example 1) in FIGS. 4 and 5. The data showed a strong impact of pressure on the rate of decrease of the conjunct polymer, with the higher reactor pressure or $H_2$ partial pressure causing a significantly higher rate of conjunct polymer removal. The 800 psig data showed that a 1 wt % level of conjunct polymer was achieved in about 10 hours at 180° C. (356° F.). One advantage to operating at higher pressures and at a more moderate temperature is that corrosion rates of the vessel used for the hydrogenation can be lower. The strong impact of the reactor pressure seen in this example was also consistent with the theory that the decrease in the content of the conjunct polymer in the acidic ionic liquid occurred by hydrogenation and hydrocracking.

Example 8: Impact of Dissolved Hydrogen Chloride in Acidic Ionic Liquid

Figure 7:
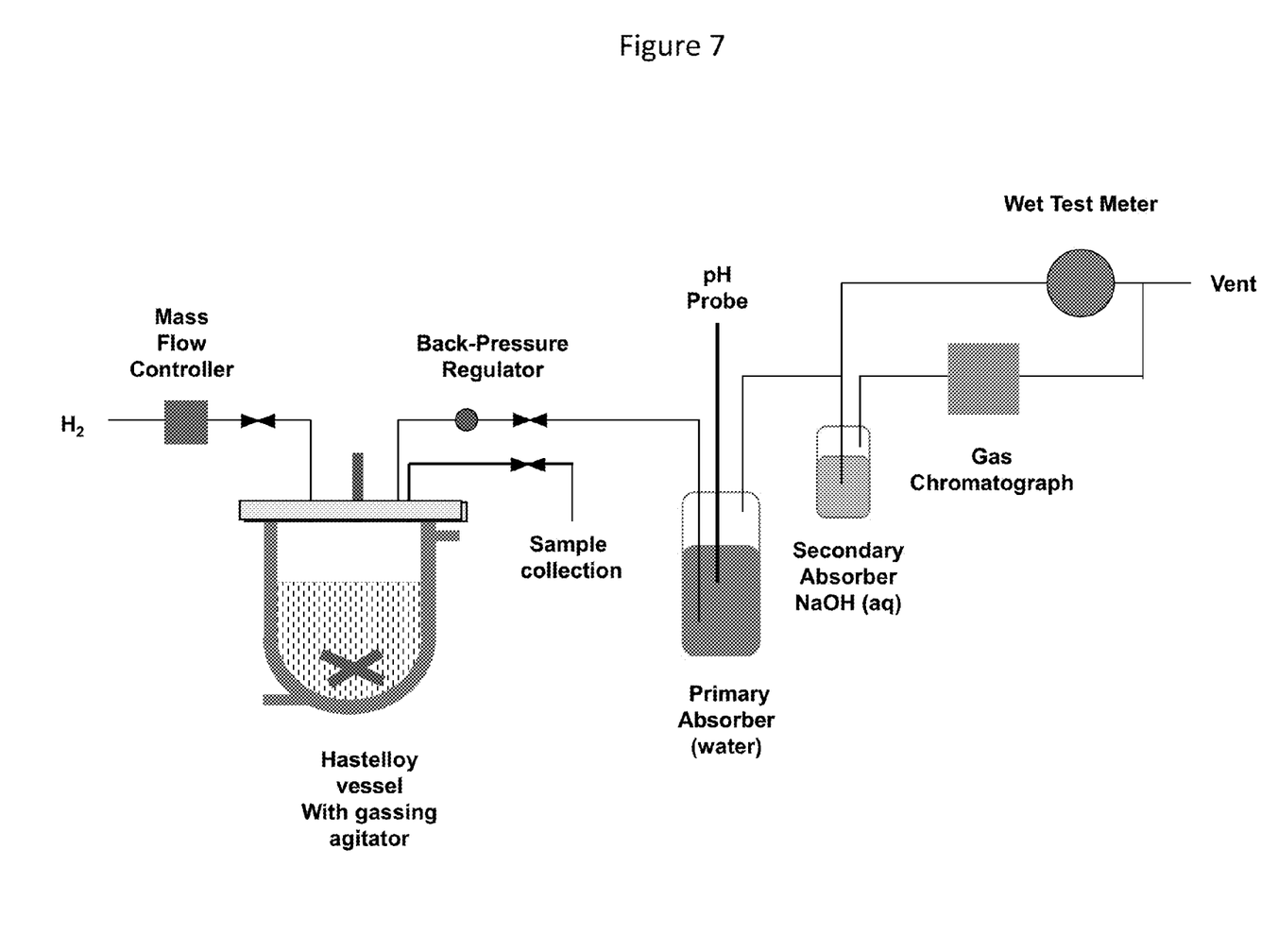
FIG. 7 is a schematic diagram of the experimental apparatus used in Example 8 in this disclosure.

The apparatus shown in FIG. 1 was modified as indicated in FIG. 7 to allow introduction of hydrogen by a flow-through method, thus allowing for continuous removal of light components during the reaction. A procedure similar to that given in Examples 2, 4, 5, and 7 was used, except that hydrogen gas was introduced via a mass flow controller and the reactor pressure was controlled using a back-pressure regulator. Hydrogen chloride content in the offgas was monitored by measuring the pH of the absorbing water solution as a function of time using a pH probe immersed in this solution.

Figure 8:
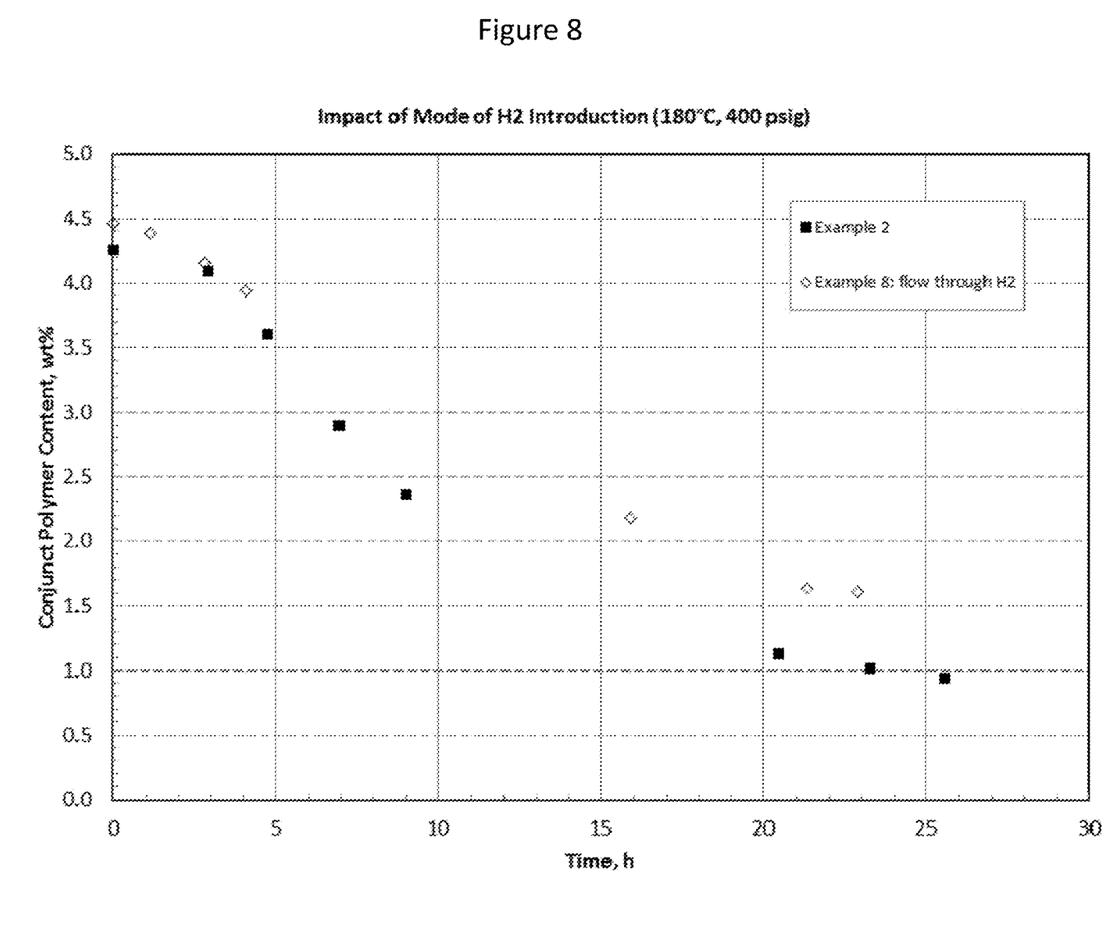
FIG. 8 is a graph showing the impact of the mode of hydrogen introduction on conjunct polymer content over time, and includes results from Example 2 and Example 8.

As conversion of conjunct polymer is known to produce hydrogen chloride, which could impact the acidic character of acidic ionic liquid, it was desired to evaluate the impact of hydrogen chloride on conjunct polymer removal. The data in FIG. 8 compared this Example 8 experiment with that from Example 2 and indicated that the decrease in the content of the conjunct polymer in the acidic ionic liquid was slower when hydrogen chloride was continuously removed from the reaction mixture.

This example indicated that modulation of the acidity of the acidic ionic liquid by dissolved hydrogen chloride can be an important parameter in conjunct polymer removal in the absence of a hydrogenation/hydrocracking catalyst.

Our examples above have shown that the conjunct polymer content in a spent acidic ionic liquid catalyst can be decreased effectively by hydrogenating and hydrocracking in the complete absence of a solid hydrogenation catalyst. In the absence of a solid hydrogenation catalyst, the conjunct polymer was hydrocracked to lighter molecules that were fully saturated. The reactor pressure and/or $H_2$ partial pressure of the reactor, and dissolved HCl content in the acidic ionic liquid, were both important factors affecting the rate of decrease (hydrocracking reaction rate) of the conjunct polymer. While we do not want to be bound by theory, it appears that the acidic functionality to perform the hydrocracking came from the acidic ionic liquid. Upon hydrocracking of the conjunct polymer, olefinic reaction intermediates were created. The olefinic reaction intermediates were hydrogenated with the $H_2$ gas present in the reactor. The source of the hydrogenation functionality in this catalytic reaction was not clear, but appeared to be related to the acidic ionic liquid (organo-aluminum halide) and the hydrogen chloride. The dissolved corrosion metals in the acidic ionic liquids may have contributed to the hydrogenation and production of fully saturated light hydrocarbons, however the contribution of these dissolved corrosion metals was not significant.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed. Unless otherwise specified, all percentages are in weight percent.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

The invention illustratively disclosed herein suitably may be practiced in the absence of any element which is not specifically disclosed herein.

It is claimed:

1. A process for regenerating a spent acidic ionic liquid, comprising contacting the spent acidic ionic liquid in a vessel used for the contacting with a hydrogen and without an addition of a hydrogenation catalyst or solids; wherein a content of a conjunct polymer is decreased in the spent acidic ionic liquid to produce a regenerated acidic ionic liquid.

2. The process of claim 1, wherein the contacting occurs at a temperature from 100° C. to 350° C.

3. The process of claim 1, wherein the contacting occurs in the vessel with an agitation rate of 50 to 2500 rpm.

4. The process of claim 1, wherein the contacting occurs in the vessel under a pressure of 50 to 5000 psig (446 to 34600 kpa).

5. The process of claim 1, wherein a contacting time is from 2 to 50 hours.

6. The process of claim 1, wherein the spent acidic ionic liquid comprises greater than 3 wt % of the conjunct polymer.

7. The process of claim 1, wherein the regenerated acidic ionic liquid comprises less than 1.5 wt % of the conjunct polymer.

8. The process of claim 1, wherein the spent acidic ionic liquid comprises less than 10,000 wppm corrosion metals.

9. The process of claim 1, wherein the regenerated acidic ionic liquid is effective for catalyzing a hydrocarbon conversion selected from the group consisting of an alkylation, a polymerization, a dimerization, an oligomerization, an acylation, a hydrocracking, a metathesis, a copolymerization, an isomerization, a carbonylation, a hydroformylation, a dehalogenation, a dehydration, a disproportionation, a transalkylation, and combinations thereof.

10. The process of claim 1, wherein the spent acidic ionic liquid comprises a metal halide.

11. The process of claim 1, wherein the spent acidic ionic liquid is a chloroaluminate or a bromoaluminate.

12. The process of claim 1, wherein the spent acidic ionic liquid comprises an unsubstituted or partly alkylated ammonium ion.

13. The process of claim 1, wherein paraffinic light gases are formed during the contacting.

14. The process of claim 1, wherein an extracted conjunct polymer naphtha, having between 5 and 30 carbon atoms, is produced by the contacting.

15. The process of claim 1, wherein no drying or reducing of the spent acidic ionic liquid is done before the contacting.

16. The process of claim 1, wherein no solids are formed in the vessel used for the contacting.

17. The process of claim 1, wherein an amount of a hydrogen chloride in the spent acidic ionic liquid is maintained at a level that increases a rate of decrease of the content of the conjunct polymer.

18. The process of claim 1, wherein a used vessel previously containing a solid hydrogenation catalyst is emptied of the solid hydrogenation catalyst and reused for the vessel used for the contacting.

19. The process of claim 1, additionally comprising:
   a. alkylating a mixture of one or more $C_4$-$C_7$ isoparaffins and one or more $C_2$-$C_6$ olefins in a presence of the regenerated acidic ionic liquid and an alkyl halide or a hydrogen halide, to produce an alkylate gasoline blending component, wherein a conjunct polymer is accumulated in the spent acidic ionic liquid;
   b. feeding the spent acidic ionic liquid and the hydrogen, and without the addition of the hydrogenation catalyst or the solids, to the vessel that is a regeneration reactor operated under hydrogenation conditions including a temperature from 100° C. to 350° C. and a pressure from 50 to 5000 psig (446 to 34600 kpa), wherein the content of the conjunct polymer is decreased by at least 50 wt % in the spent acidic ionic liquid and the spent acidic ionic liquid becomes the regenerated acidic ionic liquid that is used as an alkylation catalyst for the alkylating.

20. The process of claim 19, wherein an amount of a hydrogen chloride in the spent acidic ionic liquid is maintained at a level that increases a rate of decrease of the content of the conjunct polymer.

21. The process of claim 1, wherein the contacting occurs in a complete absence of an added hydrocracking catalyst or an added hydrogenation catalyst.

22. The process of claim 1, wherein a hydrogen chloride is formed during the contacting and an amount of the hydrogen chloride in an offgas from the vessel is monitored during the contacting.

23. The process of claim 17, wherein a back-pressure regulator is used to maintain the amount of the hydrogen chloride in the spent acidic ionic liquid.

\* \* \* \* \*